(12) United States Patent
Lucero et al.

(10) Patent No.: US 6,698,697 B1
(45) Date of Patent: Mar. 2, 2004

(54) WRIST SUPPORT DEVICE

(76) Inventors: Anthony Lucero, 950 W. Sneed Rd., French Camp, CA (US) 95231; Sharon Lucero, 950 W. Sneed Rd., French Camp, CA (US) 95231

( * ) Notice: Subject to any disclaimer, the term of this patent is extended or adjusted under 35 U.S.C. 154(b) by 0 days.

(21) Appl. No.: 10/314,080

(22) Filed: Dec. 6, 2002

(51) Int. Cl.[7] .............................................. B43L 15/00
(52) U.S. Cl. .................................................. 248/118.5
(58) Field of Search .......................... 248/118.5, 118, 248/118.1; 400/715; D14/460

(56) References Cited

U.S. PATENT DOCUMENTS

| | | | | |
|---|---|---|---|---|
| 8,065 | A | * | 4/1851 | Goshon et al. .......... 248/118.5 |
| 89,142 | A | * | 4/1869 | Gorsline .................... 34/95.2 |
| 986,620 | A | | 3/1911 | Ballou |
| 1,510,877 | A | | 10/1924 | Weidenmann |
| 1,522,652 | A | * | 1/1925 | Setrakian ................. 248/118.5 |
| 3,453,751 | A | * | 7/1969 | Kuhman .................... 434/166 |
| D357,010 | S | | 4/1995 | Dickerson et al. |
| 5,439,192 | A | | 8/1995 | King |
| 5,472,161 | A | | 12/1995 | Krukovsky |
| 5,925,007 | A | * | 7/1999 | Ashline ....................... 602/21 |
| 6,032,913 | A | | 3/2000 | Dawson |
| 6,154,199 | A | | 11/2000 | Butler |

* cited by examiner

Primary Examiner—Ramon O Ramirez

(57) ABSTRACT

A wrist support device for supporting the wrist of user while using a mouse. The wrist support device includes a cradle portion being designed for being positioned against the wrist of the user whereby the cradle portion supports the wrist of the user. A securing portion is coupled to the cradle portion. The securing portion is designed for being extended around the wrist of the user for securing the cradle portion to wrist of the user. A gliding assembly is coupled to the cradle portion whereby the gliding assembly is positioned opposite the wrist of the user. The gliding assembly is designed for gliding across a support surface whereby the gliding assembly maintains a substantially aligned arrangement between the wrist and hand of the user for reducing stress on the wrist of the user.

20 Claims, 6 Drawing Sheets

WRIST SUPPORT DEVICE

BACKGROUND OF THE INVENTION

1. Field of the Invention

The present invention relates to portable wrist supports and more particularly pertains to a new wrist support device for supporting the wrist of user while using a mouse.

2. Description of the Prior Art

The use of portable wrist supports is known in the prior art. U.S. Pat. No. 5,472,161 describes a device for supporting the wrist of a user while using a keyboard. Another type of portable wrist support is U.S. Pat. No. 1,510,877 having a wrist support strapped to the wrist of the user to support the wrist of the user when the user is writing. U.S. Pat. No. 986,620 has a pad being strapped to the wrist of user to support the wrist when the user is writing. U.S. Pat. No. 6,154,199 has a article worn over the hand of the user that acts as an input device for a computer. U.S. Pat. No. 5,439,192 has a device worn on the hand for supporting the wrist of the user while using a keyboard. U.S. Pat. No. Des. 357,010 shows a rolling wrist support.

While these devices fulfill their respective, particular objectives and requirements, the need remains for a device that has certain improved features allowing for changing of the height between the wrist of the user and the support surface.

SUMMARY OF THE INVENTION

The present invention meets the needs presented above by providing spacer portions that are selectively couplable between the gliding assembly and the cradle portion to adjust the height at which the wrist is supported.

Still yet another object of the present invention is to provide a new wrist support device that has a gliding device to allow smooth movement across a support surface.

To this end, the present invention generally comprises a cradle portion being designed for being positioned against the wrist of the user whereby the cradle portion supports the wrist of the user. A securing portion is coupled to the cradle portion. The securing portion is designed for being extended around the wrist of the user for securing the cradle portion to wrist of the user. A gliding assembly is coupled to the cradle portion whereby the gliding assembly is positioned opposite the wrist of the user. The gliding assembly is designed for gliding across a support surface whereby the gliding assembly maintains a substantially aligned arrangement between the wrist and hand of the user for reducing stress on the wrist of the user.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
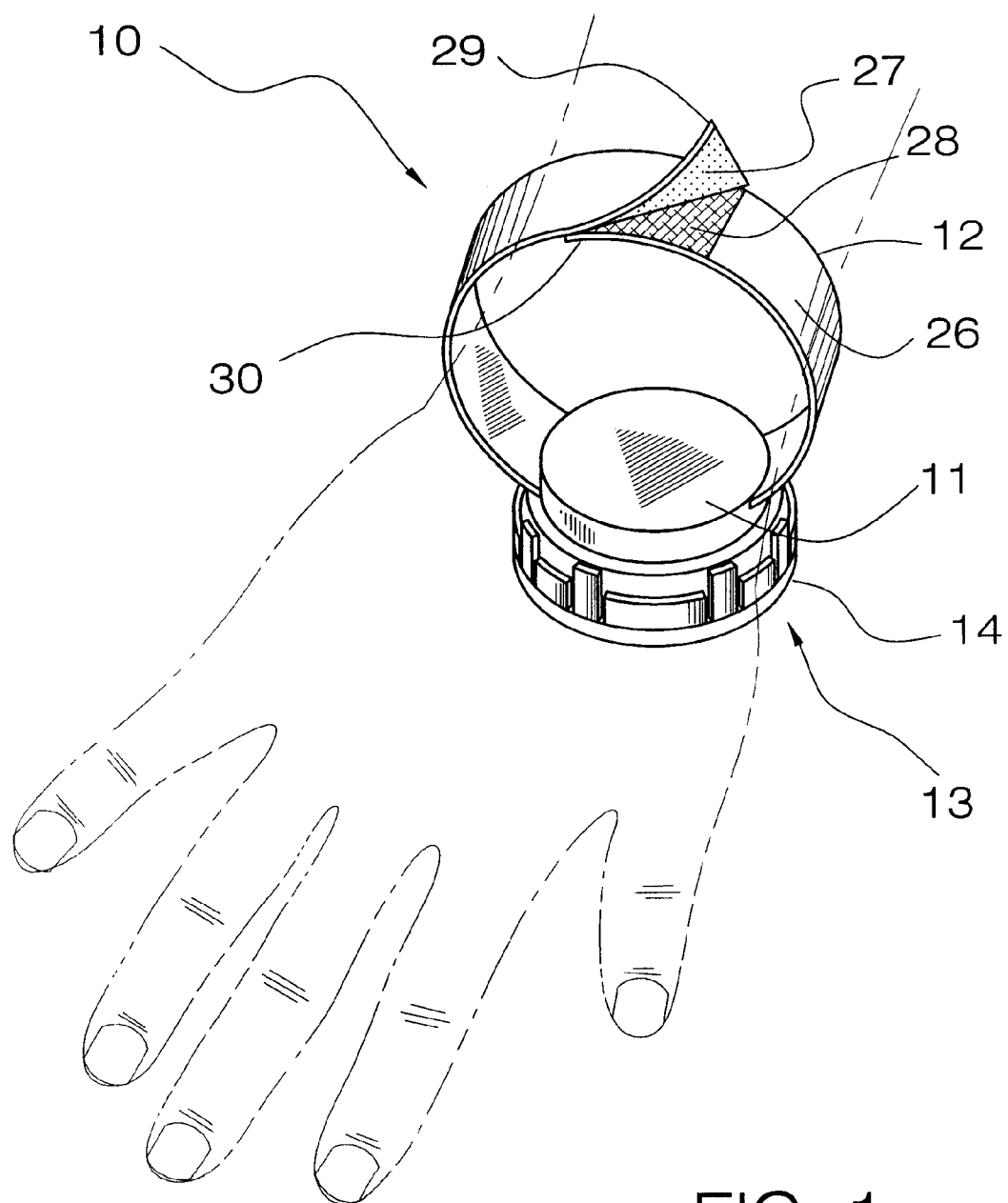
FIG. 1 is a perspective view of a new wrist support device according to the present invention shown in use.
Figure 2:
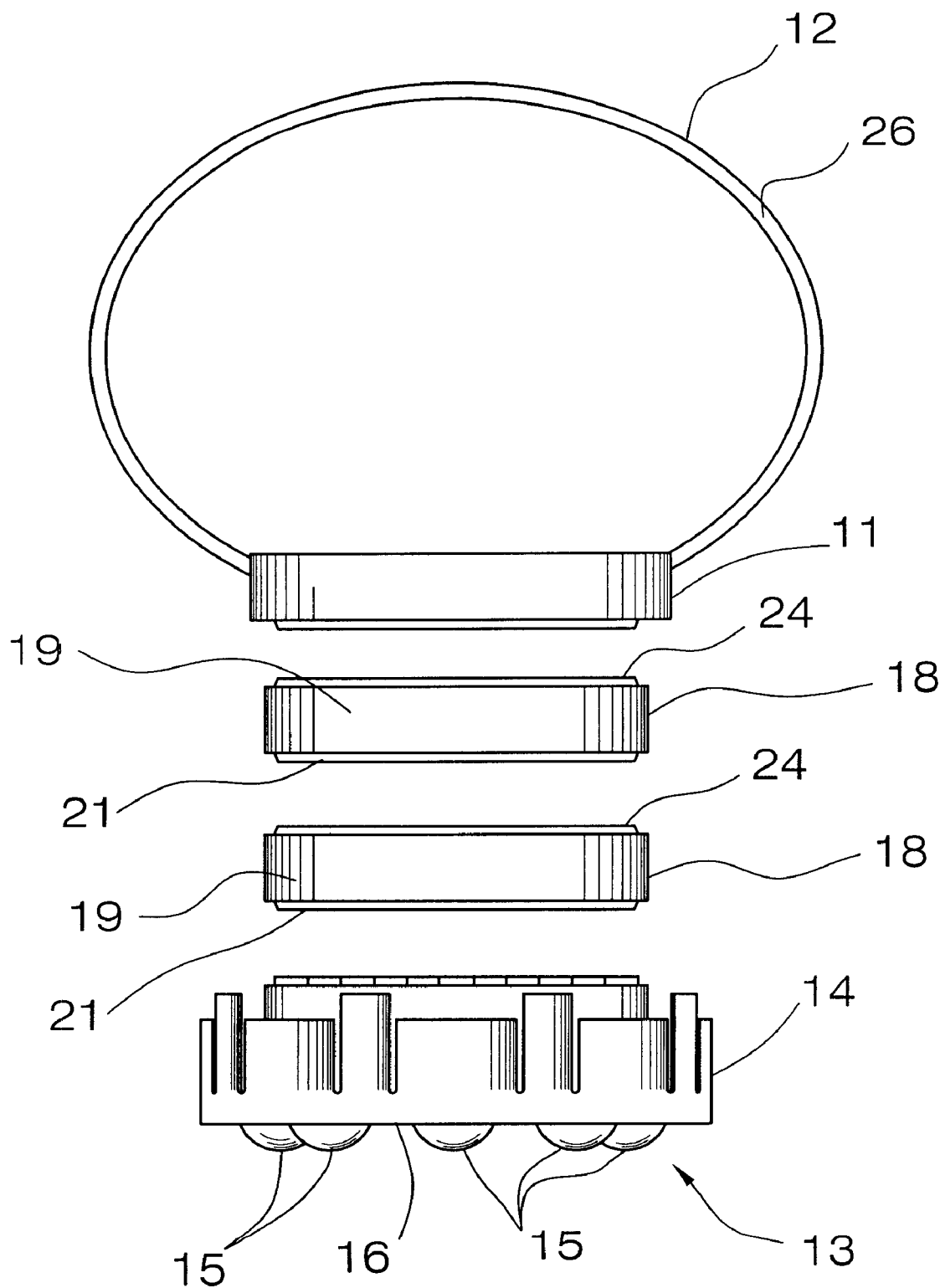
FIG. 2 is an exploded side view of the present invention.
Figure 3:
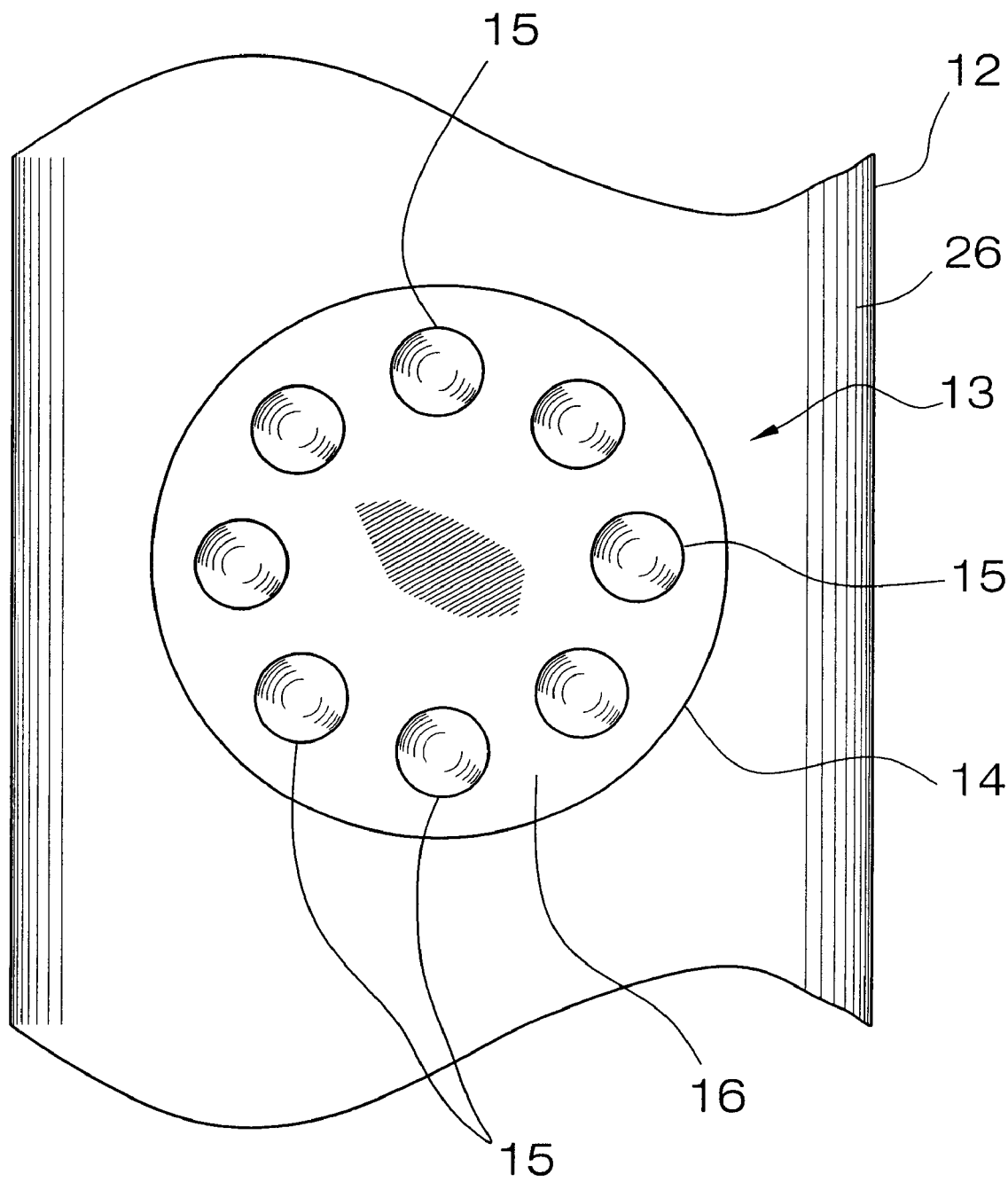
FIG. 3 is a bottom view of the present invention.
Figure 4:
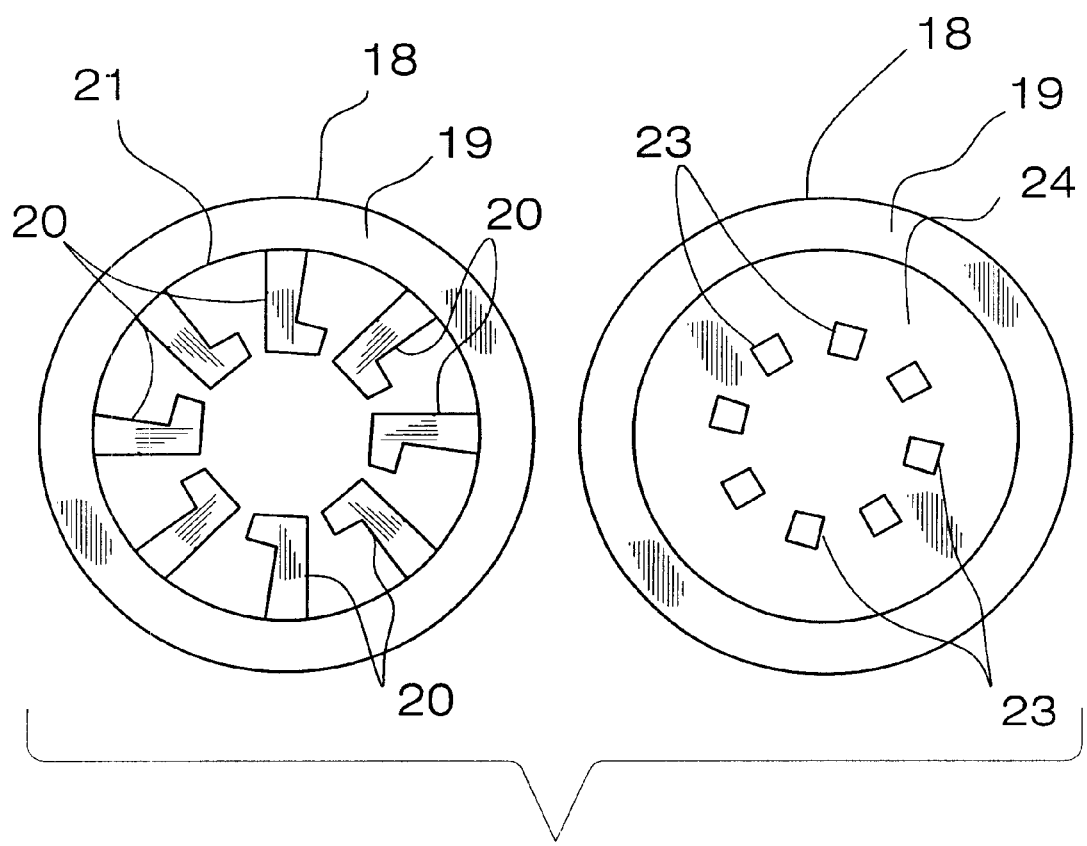
FIG. 4 is a plan view of two spacer portions the present invention shown separated.
Figure 5:
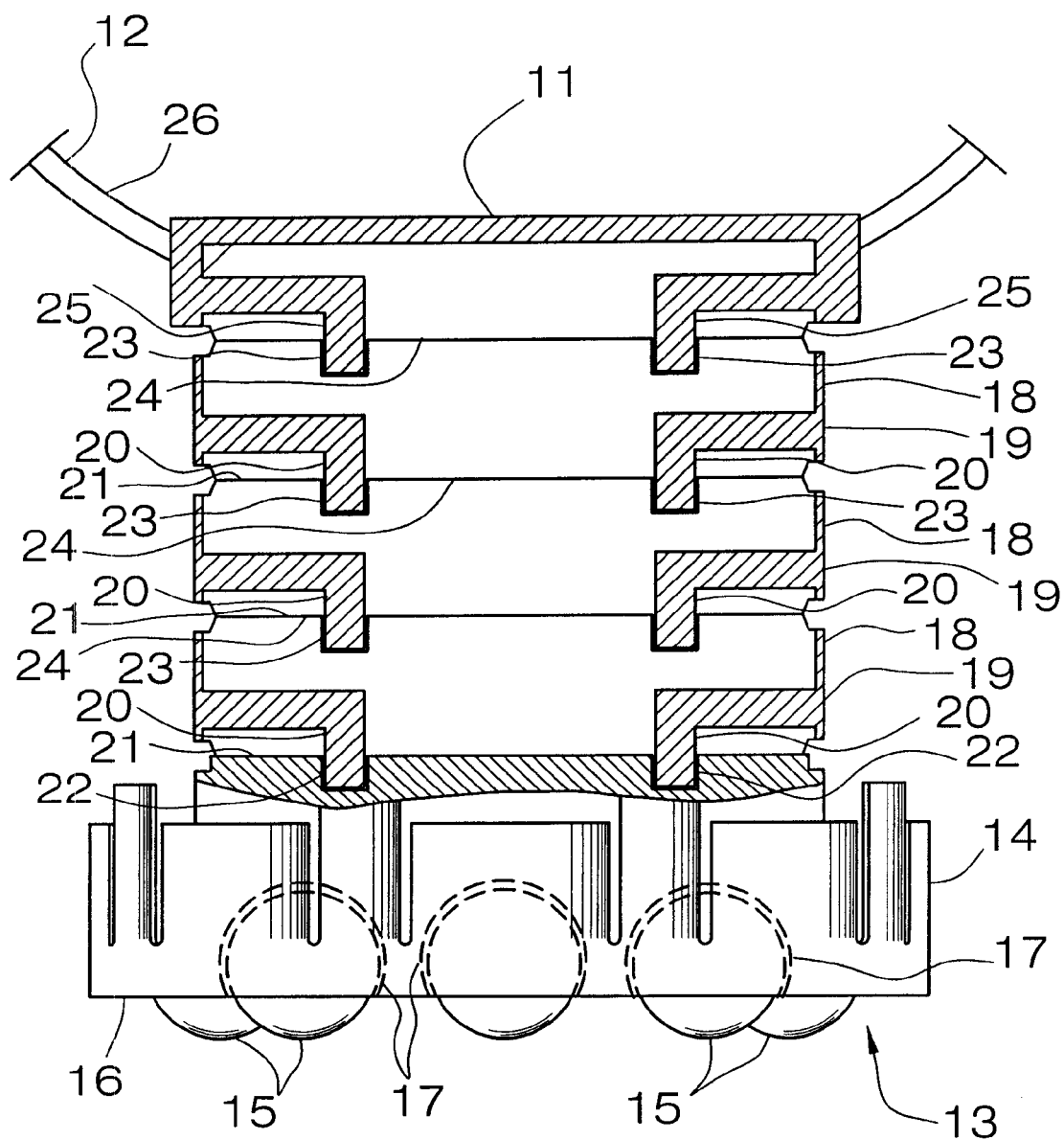
FIG. 5 is a partial cross-sectional side view of the present invention.

With reference now to the drawings, and in particular to FIGS. 1 through 6 thereof, a new wrist support device embodying the principles and concepts of the present invention and generally designated by the reference numeral 10 will be described.

As best illustrated in FIGS. 1 through 6, the wrist support device 10 generally comprises a cradle portion 11 being designed for being positioned against the wrist of the user whereby the cradle portion 11 supports the wrist of the user.

A securing portion 12 is coupled to the cradle portion 11. The securing portion 12 is designed for being extended around the wrist of the user for securing the cradle portion 11 to wrist of the user.

A gliding assembly 13 is coupled to the cradle portion 11 whereby the gliding assembly 13 is positioned opposite the wrist of the user. The gliding assembly 13 is designed for gliding across a support surface whereby the gliding assembly 13 maintains a substantially aligned arrangement between the wrist and hand of the user for reducing stress on the wrist of the user.

The gliding assembly 13 comprises a base portion 14. The base portion 14 is coupled to the cradle portion 11. The gliding assembly 13 comprises a plurality of gliding members 15. Each of the gliding members 15 is coupled to a bottom face 16 of the base portion 14. Each of the gliding members 15 is designed for gliding across the support surface for permitting repositioning of the wrist with respect to the support surface.

The base portion 14 the gliding assembly 13 comprises a plurality of arcuate depressions 17. Each of the arcuate depressions 17 extends into the base portion 14 from the bottom face 16 of the gliding assembly 13. Each of the gliding members 15 is substantially spherical whereby each of the gliding members 15 is positioned in one of the arcuate depressions 17. Each of the gliding members 15 is for rolling in the associated one of the arcuate depressions 17 when the gliding members 15 are positioned on the support surface.

At least one spacer portion 18 is selectively couplable between the cradle portion 11 and the gliding assembly 13. The spacer portion 18 is designed for increasing a distance between the wrist and the support surface when the spacer portion 18 is coupled between the cradle portion 11 and the gliding assembly 13. The spacer portion 18 may comprise a rigid material, such as metal or plastic.

The spacer portion 18 comprises a main portion 19. The spacer portion 18 comprises a plurality of spacer locking members downwardly extending from a bottom surface of the main portion 19 of the spacer portion 18. Each of the spacer locking members 20 selectively engages one of a plurality of gliding locking apertures 22 23 of the gliding assembly 13 for securing the spacer portion 18 to the gliding assembly 13. The spacer portion 18 has a plurality of spacer locking apertures 23 extending into the main portion 19 from a top surface 24 of the main portion 19. Each of the spacer locking apertures 23 selectively receives one of a plurality of cradle locking members 25 of the cradle portion 11 for securing the cradle portion 11 to the spacer portion 18.

The securing portion 12 comprises a band member 26. The band member 26 is coupled to the cradle portion 11. The band member 26 is designed for being selectively positionable around the wrist of the user whereby the band member 26 secures the cradle portion 11 to the wrist of the user. The band member 26 may comprise elastic so the band member is expandable to fit onto the wrist and then constricts against the wrist to secure the cradle portion to wrist of the user.

The securing portion 12 comprises a first fastener member 27 and a second fastener member 28. The first fastener member 27 is coupled to a first end 29 of the band member 26. The second fastener member 28 is coupled to a second end 30 of the band member 26. The first fastener member 27 is complimentary to the second fastener member 28 whereby the first fastener member 27 is selectively couplable to the second fastener member 28 for securing the first end 29 of the band member 26 to the second end 30 of the band member 26 when the band member 26 is positioned around the wrist of the user. The first fastener member 27 and the second fastener member 28 may comprise hook and loop fastener, a snap fastener or a button and button hole to allow securing of the band member 26 to the wrist of the user.

Figure 6:
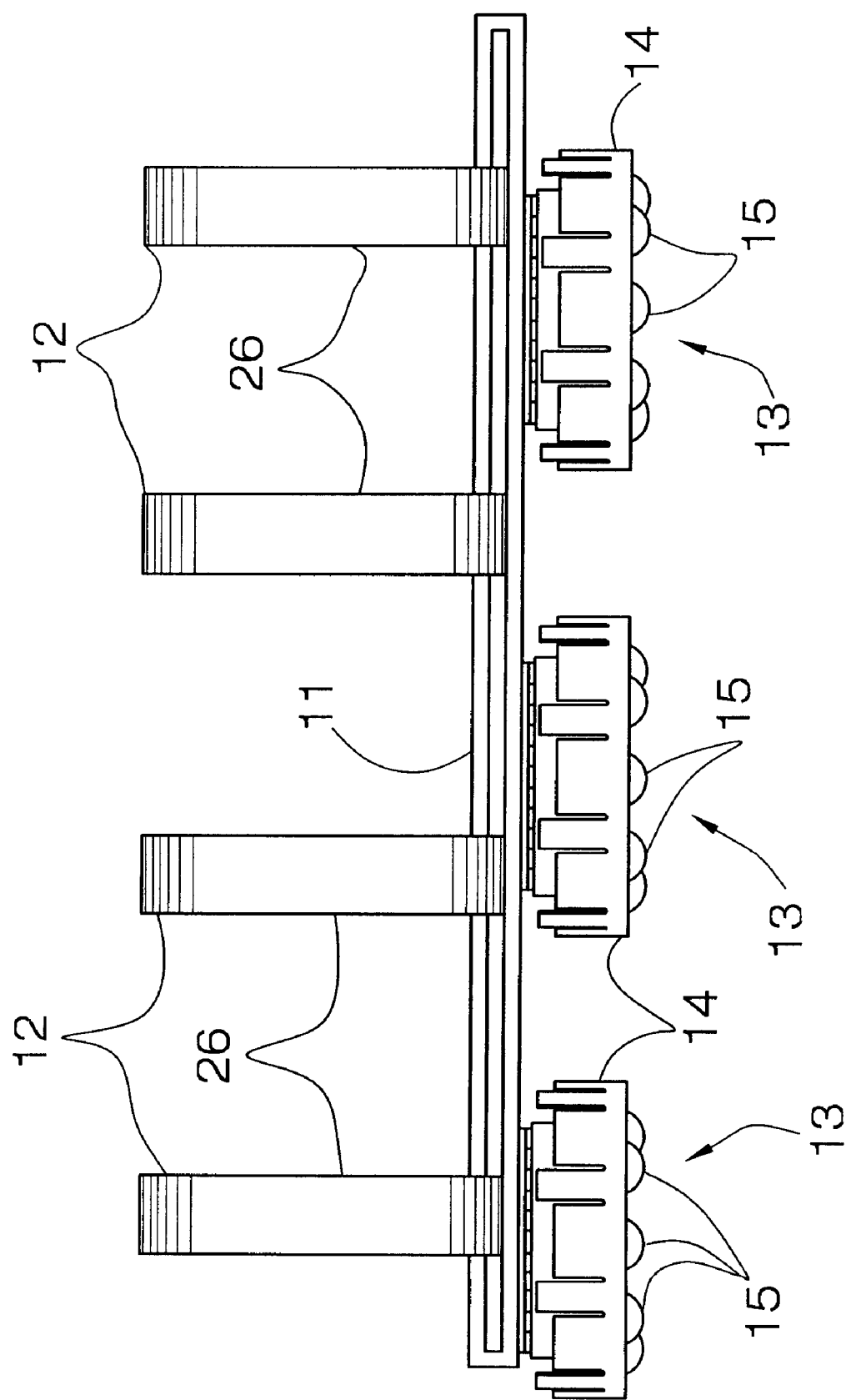
FIG. 6 is a side view of an alternate embodiment of the resent invention.

In and embodiment, as shown in FIG. 6, the cradle portion 11 is designed for being positioned under the forearm of the user. Each of a plurality of securing portions 12 is coupled to the cradle portion 11. Each of the securing portions 12 is designed for being extended around the forearm of the user for securing the cradle portion 11 to forearm of the user.

Each of a plurality of gliding assemblies 13 is coupled to the cradle portion 11 whereby the gliding assemblies 13 are positioned opposite the forearm of the user. The gliding assemblies 13 are designed for gliding across the support surface whereby the gliding assemblies 13 maintain a substantially aligned arrangement between the forearm and hand of the user for reducing stress on the forearm of the user.

Each of the gliding assemblies 13 comprises a base portion 14. The base portion 14 is coupled to the cradle portion 11. Each the gliding assemblies 13 comprises a plurality of gliding members 15. Each of the gliding members 15 is coupled to a bottom face 16 of the base portion 14. Each of the gliding members 15 is designed for gliding across the support surface for permitting repositioning of the forearm with respect to the support surface.

The base portion 14 of each of the gliding assemblies 13 comprises a plurality of arcuate depressions 17. Each of the arcuate depressions 17 extending into the base portion 14 from the bottom face 16 of the associated one of the gliding assemblies 13. Each of the gliding members 15 is substantially spherical whereby each of the gliding members 15 is positioned in one of the arcuate depressions 17. Each of the gliding members 15 is for rolling in the associated one of the arcuate depressions 17 when the gliding members 15 are positioned on the support surface.

A plurality of spacer portions 18 are selectively couplable between the cradle portion 11 and an associated one of the gliding assemblies 13. Each of the spacer portions 18 is designed for increasing a distance between the forearm and the support surface when the spacer portions 18 are coupled between the cradle portion 11 and the associated one of the gliding assemblies 13.

Each of the spacer portions 18 comprises a main portion 19. Each of the spacer portions 18 comprises a plurality of spacer locking members 20 downwardly extending from a bottom surface of the main portion 19 of the associated one of the spacer portions 18. Each of the spacer locking members 20 selectively engages one of a plurality of gliding locking apertures 22 23 of the associated one of the gliding assemblies 13 for securing the spacer portions 18 to one of the gliding assemblies 13. Each of the spacer portions 18 has a plurality of spacer locking apertures 23 extending into the main portion 19 from a top surface 24 of the main portion 19. Each of the spacer locking apertures 23 selectively receives one of a plurality of cradle locking members 25 of the cradle portion 11 for securing the cradle portion 11 to one of the spacer portions 18.

Each of the securing portions 12 comprises a band member 26. The band member 26 is coupled to the cradle portion 11. The band member 26 is designed for being selectively positionable around the forearm of the user whereby the band member 26 secures the cradle portion 11 to the forearm of the user.

Each of the securing portions 12 comprises a first fastener member 27 and a second fastener member 28. The first fastener member 27 is coupled to a first end 29 of the band member 26. The second fastener member 28 is coupled to a second end 30 of the band member 26. The first fastener member 27 is complimentary to the second fastener member 28 whereby the first fastener member 27 is selectively couplable to the second fastener member 28 for securing the first end 29 of the band member 26 to the second end 30 of the band member 26 when the band member 26 is positioned around the forearm of the user.

In use, the user places the cradle portion 11 against the inside of the wrist. The band member 26 of the securing portion 12 is then extended around the wrist and the first fastener member 27 is coupled to the second fastener member 28 the secure the band member 26 around the wrist. A spacer portion 18 can then be coupled to the cradle portion 11 and a gliding assembly 13 can be coupled to the spacer portion 18. The gliding assembly 13 is then placed on the support surface to support the wrist of the user while the user is using a mouse.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A wrist support device for supporting a wrist of a user while using a mouse, the wrist support device comprising:
   a cradle portion being adapted for being positioned against the wrist of the user such that said cradle portion supports the wrist of the user;

at least one securing portion being coupled to said cradle portion, said securing portion being adapted for being extended around the wrist of the user for securing said cradle portion to wrist of the user;

at least one gliding assembly being coupled to said cradle portion such that said gliding assembly is positioned opposite the wrist of the user, said gliding assembly being adapted for gliding across a support surface such that said gliding assembly maintains a substantially aligned arrangement between the wrist and hand of the user for reducing stress on the wrist of the user; and said gliding assembly comprising a plurality of gliding locking apertures, each of said gliding locking apertures selectively receiving one of a plurality of cradle locking members of said cradle portion for securing said gliding assembly to said cradle portion.

2. The support device as set forth in claim 1, further comprising:

said gliding assembly comprising a base portion, said base portion being coupled to said cradle portion, said gliding assembly comprising a plurality of gliding members, each of said gliding members being coupled to a bottom face of said base portion, each of said gliding members being adapted for gliding across the support surface for permitting repositioning of the wrist with respect to the support surface.

3. The support device as set forth in claim 2, further comprising:

said base portion of said gliding assembly comprising a plurality of arcuate depressions, each of said arcuate depressions extending into said base portion from said bottom face of said gliding assembly, each of said gliding members being substantially spherical such that each of said gliding members is positioned in one of said arcuate depressions, each of said gliding members being for rolling in the associated one of said arcuate depressions when said gliding members are positioned on the support surface.

4. The support device as set forth in claim 1, further comprising:

at least one spacer portion being selectively couplable between said cradle portion and said gliding assembly, said spacer portion being adapted for increasing a distance between the wrist and the support surface when said spacer portion is coupled between said cradle portion and said gliding assembly.

5. The support device as set forth in claim 4, further comprising:

said spacer portion comprising a main portion, said spacer portion comprising a plurality of spacer locking members downwardly extending from a bottom surface of said main portion of said spacer portion, each of said spacer locking members selectively engaging one of a plurality of gliding locking apertures of said gliding assembly for securing said spacer portion to said glider assembly, said spacer portion having a plurality of spacer locking apertures extending into said main portion from a top surface of said main portion, each of said spacer locking apertures selectively receiving one of a plurality of cradle locking members of said cradle portion for securing said cradle portion to said spacer portion.

6. The support device as set forth in claim 1, further comprising:

said securing portion comprising a band member, said band member being coupled to said cradle portion, said band member being adapted for being selectively positionable around the wrist of the user such that said band member secures said cradle portion to the wrist of the user.

7. The support device as set forth in claim 6, further comprising:

said securing portion comprising a first fastener member and a second fastener member, said first fastener member being coupled to a first end of said band member, said second fastener member being coupled to a second end of said band member, said first fastener member being complimentary to said second fastener member such that said first fastener member is selectively couplable to said second fastener member for securing said first end of said band member to said second end of said band member when the band member is positioned around the wrist of the user.

8. The support device as set forth in claim 1, further comprising:

said cradle portion being elongated such that said cradle portion is adapted for being positioned under the forearm of the user;

said securing portion comprising a plurality of securing portions, each of said securing portions being coupled to said cradle portion, each of said securing portions being adapted for being extended around the forearm of the user for securing said cradle portion to forearm of the user; and said gliding assembly comprising a plurality of gliding assemblies each of said gliding assemblies being coupled to said cradle portion such that said gliding assemblies are positioned opposite the forearm of the user, said gliding assemblies being adapted for gliding across the support surface such that said gliding assemblies maintain a substantially aligned arrangement between the forearm and hand of the user for reducing stress on the forearm of the user.

9. The support device as set forth in claim 8, further comprising:

each of said securing portions comprising a band member, said band member being coupled to said cradle portion, said band member being adapted for being selectively positionable around the forearm of the user such that said band member secures said cradle portion to the forearm of the user; and each of said securing portions comprising a first fastener member and a second fastener member, said first fastener member being coupled to a first end of said band member, said second fastener member being coupled to a second end of said band member, said first fastener member being complimentary to said second fastener member such that said first fastener member is selectively couplable to said second fastener member for securing said first end of said band member to said second end of said band member when the band member is positioned around the forearm of the user.

10. The support device as set forth in claim 8, further comprising:

each of said gliding assemblies comprising a base portion, said base portion being coupled to said cradle portion, each said gliding assemblies comprising a plurality of gliding members, each of said gliding members being coupled to a bottom face of said base portion, each of said gliding members being adapted for gliding across the support surface for permitting repositioning of the forearm with respect to the support surface; and said base portion of each of said gliding assemblies comprising a plurality of arcuate depressions, each of said arcuate depressions extending into said base portion from said bottom face of the associated one of said gliding assemblies, each of said gliding members being substantially spherical such that each of said gliding members is positioned in one of said arcuate depressions, each of said gliding members being for rolling in the associated one of said arcuate depressions when said gliding members are positioned on the support surface.

11. The support device as set forth in claim 8, further comprising:

said cradle portion comprising a plurality of cradle locking members, each of said cradle locking members selectively engaging one of a plurality of gliding locking apertures of one of said glider assemblies for securing said gliding assemblies to said cradle portion.

12. The support device as set forth in claim 8, further comprising:

a plurality of spacer portions being selectively couplable between said cradle portion and an associated one of said gliding assemblies, each of said spacer portions being adapted for increasing a distance between the forearm and the support surface when said spacer portions are coupled between said cradle portion and the associated one of said gliding assemblies.

13. The support device as set forth in claim 12, further comprising:

each of said spacer portions comprising a main portion, each of said spacer portions comprising a plurality of spacer locking members downwardly extending from a bottom surface of said main portion of the associated one of said spacer portions, each of said spacer locking members selectively engaging one of a plurality of gliding locking apertures of the associated one of said gliding assemblies for securing said spacer portions to one of said gliding assemblies, each of said spacer portions having a plurality of spacer locking apertures extending into said main portion from a top surface of said main portion, each of said spacer locking apertures selectively receiving one of a plurality of cradle locking members of said cradle portion for securing said cradle portion to one of said spacer portions.

14. A wrist support device for supporting a wrist of a user while using a mouse, the wrist support device comprising:

a cradle portion being adapted for being positioned against the wrist of the user such that said cradle portion supports the wrist of the user;

a securing portion being coupled to said cradle portion, said securing portion being adapted for being extended around the wrist of the user for securing said cradle portion to wrist of the user;

a gliding assembly being coupled to said cradle portion such that said gliding assembly is positioned opposite the wrist of the user, said gliding assembly being adapted for gliding across a support surface such that said gliding assembly maintains a substantially aligned arrangement between the wrist and hand of the user for reducing stress on the wrist of the user;

said gliding assembly comprising a base portion, said base portion being coupled to said cradle portion, said gliding assembly comprising a plurality of gliding members, each of said gliding members being coupled to a bottom face of said base portion, each of said gliding members being adapted for gliding across the support surface for permitting repositioning of the wrist with respect to the support surface;

said base portion of said gliding assembly comprising a plurality of arcuate depressions, each of said arcuate depressions extending into said base portion from said bottom face of said gliding assembly, each of said gliding members being substantially spherical such that each of said gliding members is positioned in one of said arcuate depressions, each of said gliding members being for rolling in the associated one of said arcuate depressions when said gliding members are positioned on the support surface;

at least one spacer portion being selectively couplable between said cradle portion and said gliding assembly, said spacer portion being adapted for increasing a distance between the wrist and the support surface when said spacer portion is coupled between said cradle portion and said gliding assembly;

said spacer portion comprising a main portion, said spacer portion comprising a plurality of spacer locking members downwardly extending from a bottom surface of said main portion of said spacer portion, each of said spacer locking members selectively engaging one of a plurality of gliding locking apertures of said gliding assembly for securing said spacer portion to said glider assembly, said spacer portion having a plurality of spacer locking apertures extending into said main portion from a top surface of said main portion, each of said spacer locking apertures selectively receiving one of a plurality of cradle locking members of said cradle portion for securing said cradle portion to said spacer portion;

said securing portion comprising a band member, said band member being coupled to said cradle portion, said band member being adapted for being selectively positionable around the wrist of the user such that said band member secures said cradle portion to the wrist of the user; and said securing portion comprising a first fastener member and a second fastener member, said first fastener member being coupled to a first end of said band member, said second fastener member being coupled to a second end of said band member, said first fastener member being complimentary to said second fastener member such that said first fastener member is selectively couplable to said second fastener member for securing said first end of said band member to said second end of said band member when the band member is positioned around the wrist of the user.

15. A wrist support device for supporting a wrist of a user while using a mouse, the wrist support device comprising:

a cradle portion being adapted for being positioned against the wrist of the user such that said cradle portion supports the wrist of the user;

at least one securing portion being coupled to said cradle portion, said securing portion being adapted for being extended around the wrist of the user for securing said cradle portion to wrist of the user;

at least one gliding assembly being coupled to said cradle portion such that said gliding assembly is positioned opposite the wrist of the user, said gliding assembly being adapted for gliding across a support surface such that said gliding assembly maintains a substantially aligned arrangement between the wrist and hand of the user for reducing stress on the wrist of the user;

at least one spacer portion being selectively couplable between said cradle portion and said gliding assembly, said spacer portion being adapted for increasing a distance between the wrist and the support surface when said spacer portion is coupled between said cradle portion and said gliding assembly; and said spacer portion comprising a main portion, said spacer portion comprising a plurality of spacer locking members downwardly extending from a bottom surface of said main portion of said spacer portion, each of said spacer locking members selectively engaging one of a plurality of gliding locking apertures of said gliding assembly for securing said spacer portion to said glider assembly, said spacer portion having a plurality of spacer locking apertures extending into said main portion from a top surface of said main portion, each of said spacer locking apertures selectively receiving one of a plurality of cradle locking members of said cradle portion for securing said cradle portion to said spacer portion.

16. The support device as set forth in claim 15, further comprising:

said gliding assembly comprising a base portion, said base portion being coupled to said cradle portion, said gliding assembly comprising a plurality of gliding members, each of said gliding members being coupled to a bottom face of said base portion, each of said gliding members being adapted for gliding across the support surface for permitting repositioning of the wrist with respect to the support surface.

17. The support device as set forth in claim 16, further comprising:

said base portion of said gliding assembly comprising a plurality of arcuate depressions, each of said arcuate depressions extending into said base portion from said bottom face of said gliding assembly, each of said gliding members being substantially spherical such that each of said gliding members is positioned in one of said arcuate depressions, each of said gliding members being for rolling in the associated one of said arcuate depressions when said gliding members are positioned on the support surface.

18. The support device as set forth in claim 15, further comprising:

said securing portion comprising a band member, said band member being coupled to said cradle portion, said band member being adapted for being selectively positionable around the wrist of the user such that said band member secures said cradle portion to the wrist of the user.

19. The support device as set forth in claim 17, further comprising:

said securing portion comprising a first fastener member and a second fastener member, said first fastener member being coupled to a first end of said band member, said second fastener member being coupled to a second end of said band member, said first fastener member being complimentary to said second fastener member such that said first fastener member is selectively couplable to said second fastener member for securing said first end of said band member to said second end of said band member when the band member is positioned around the wrist of the user.

20. The support device as set forth in claim 15, further comprising:

said cradle portion being elongated such that said cradle portion is adapted for being positioned under the forearm of the user;

said securing portion comprising a plurality of securing portions, each of said securing portions being coupled to said cradle portion, each of said securing portions being adapted for being extended around the forearm of the user for securing said cradle portion to forearm of the user; and said gliding assembly comprising a plurality of gliding assemblies, each of said gliding assemblies being coupled to said cradle portion such that said gliding assemblies are positioned opposite the forearm of the user, said gliding assemblies being adapted for gliding across the support surface such that said gliding assemblies maintain a substantially aligned arrangement between the forearm and hand of the user for reducing stress on the forearm of the user.

\* \* \* \* \*